United States Patent
Ishikawa et al.

(10) Patent No.: US 6,191,305 B1
(45) Date of Patent: Feb. 20, 2001

(54) PREPARATION OF TETRAESTER OF 3, 3', 4, 4', - BIPHENYLTETRACARBOXYLIC ACID

(75) Inventors: Akira Ishikawa; Hiroto Mitsui; Kiyotaka Akao; Norihisa Komoda, all of Ube (JP)

(73) Assignee: Ube Industries, Ltd., Yamaguchi (JP)

( * ) Notice: Under 35 U.S.C. 154(b), the term of this patent shall be extended for 0 days.

(21) Appl. No.: 09/418,654

(22) Filed: Oct. 15, 1999

(30) Foreign Application Priority Data

Oct. 15, 1998 (JP) .................................................. 10-293907
Aug. 9, 1999 (JP) .................................................. 11-225382

(51) Int. Cl.$^7$ .................................................. C07C 69/76
(52) U.S. Cl. ................................................ 560/76; 560/96
(58) Field of Search ......................................... 560/76, 96

(56) References Cited

U.S. PATENT DOCUMENTS 5,081,281 * 1/1992 Ding et al. .

FOREIGN PATENT DOCUMENTS

| 57-062241 | * | 4/1982 | (JP) . |
| 01168786 | * | 7/1989 | (JP) . |
| 01175987 | * | 7/1989 | (JP) . |
| 02197589 | * | 8/1990 | (JP) . |

* cited by examiner

Primary Examiner—Paul J. Killos
(74) Attorney, Agent, or Firm—Reed Smith LLP

(57) ABSTRACT

A tetraester of 3,3',4,4'-biphenyltetracarboxylic acid is advantageously prepared by a process composed of a step of dimerizing an o-phthalic diester in the presence of a catalyst comprising a powdery palladium salt having a specific surface area of at least 0.5 m$^2$/g and a basic bidentate ligand compound and one or more steps of continuing the dimerization after supplemental addition of at least one of the powdery palladium salt and the basic bidentate ligand compound.

9 Claims, No Drawings

PREPARATION OF TETRAESTER OF 3, 3', 4, 4', - BIPHENYLTETRACARBOXYLIC ACID

FIELD OF THE INVENTION

The present invention relates a process for preparing a tetraester of 3,3',4,4'-biphenyltetracarboxylic acid.

BACKGROUND OF THE INVENTION

A process for preparing a tetraester of 3,3',4,4'-biphenyltetracarboxylic acid which comprises a step of dimerizing an o-phthalic diester in the presence of a catalyst comprising a powdery palladium salt and a basic bidentate ligand compound and one or more steps of continuing the dimerization after supplemental addition of at least one of the powdery palladium salt and the basic bidentate ligand compound is already known.

The above-mentioned process is advantageous in that it gives an increased ratio of dimerization (or conversion) of o-phthalic diester and an increased selectivity to the desired tetraester of 3,3',4,4'-biphenyltetracarboxylic acid.

For instance, according to a working example of Japanese Patent Publication No. 5-73733, the ratio of dimerization (conversion) of o-phthalic diester is 23%, and the selectivity to tetraester of 3,3',4,4'-biphenyltetracarboxylic acid is 79%. It is noted, however, that a catalyst yield (i.e., yield based on the amount of Pd employed) is approximately as much as approximately 100 molar times. This catalyst yield is not satisfactory. Moreover, in the process, not a small amount of metallic palladium is deposited on a wall of a reaction vessel. The deposition of the metallic palladium adversely effects the yield of the desired product and disturbs continuing a reaction for a long period of time.

SUMMARY OF THE INVENTION

It is an object of the present invention to provide an improved process for the preparation of a tetraester of 3,3',4,4'-biphenyltetracarboxylic acid not only at a high conversion ratio and at a high selectivity to the desired product but also at a high catalyst yield (i.e., yield per Pd).

It is another object of the invention to provide an improved process for preparing a tetraester of 3,3',4,4'-biphenyltetracarboxylic acid which produces a reduced metallic palladium deposition.

There is provided by the invention a process for the preparation of a tetraester of 3,3',4,4'-biphenyltetracarboxylic acid which comprises a step of dimerizing an o-phthalic diester in the presence of a catalyst comprising a powdery palladium salt having a specific surface area of at least 0.5 m$^2$/g and a basic bidentate ligand compound and one or more steps of continuing the dimerization after supplemental addition of at least one of the powdery palladium salt and the basic bidentate ligand compound.

DETAILED DESCRIPTION OF THE INVENTION

Preferred embodiments of the invention are described below.

(1) The powdery palladium salt employed has a specific surface area of 0.7 to 20 m$^2$/g.

(2) The powdery palladium salt employed has a specific surface area of 1.0 to 10 m$^2$/g.

(3) The powdery palladium salt is a palladium acetate powder.

(4) The basic bidentate ligand compound is 1,10-phenanthroline.

(5) The catalyst is formed of a powdery palladium salt and a basic bidentate ligand compound and further a copper salt, specifically copper acetylacetonate.

(6) Both of the powdery palladium salt and the basic bidentate ligand compound are supplemented in the continued step.

(7) The supplemental addition of at least one of the powdery palladium salt and the basic bidentate ligand compound in the second step is made to a portion of a reaction mixture comprising the o-phthalic diester, the catalyst, and the prepared tetraester of 3,3',4,4'-biphenyltetracarboxylic acid which is separated from other portion of the reaction mixture and then combined with the other portion of the reaction mixture.

The process of the invention can be preferably performed in a reaction vessel for dimerization reaction which is equipped with a stirrer, an inlet for starting materials, an outlet for products, a air-supplying pipe, and a reaction mixture-circulating system provided with a circulating pump and a catalyst incorporation apparatus.

In the dimerization reaction of the process of the invention, the catalyst to be employed in the first step is produced from a powdery palladium salt and a basic bidentate ligand compound. The powdery palladium salt has a specific surface area of not less than 0.5 m$^2$/g, preferably in the range of 0.7 to 20 m$^2$/g, more preferably 1.0 to 10 m$^2$/g. The powdery palladium salt preferably contains Pt, Fe and Cu in a total amount of less than 0.01 wt. %, more preferably in the range of 0.00001 to 0.01 wt. %. The powdery palladium salt preferably is soluble in an organic solvent such as acetone and preferably contains almost no water content such as less than 0.4 wt. % (measured at room temperature through 120° C.). The catalyst preferably comprises a copper salt.

In the dimerization reaction of the first step, the powdery palladium salt is preferably used in the range of 0.00001 to 0.005 molar amount based on one molar amount of the o-phthalic diester. For one molar amount of the powdery palladium salt, the basic bidentate ligand compound is preferably used in the range of 0.5 to 4 molar amounts. The copper salt is preferably used in the range of 0.01 to 5 molar amounts based on one molar amount of the powdery palladium salt.

The dimerization reaction in the first step is preferably performed by heating an o-phthalic diester and the catalyst composition to a temperature of approximately 140 to 260° C. under introducing a molecular oxygen-containing gas such as air, to produce the desired tetraester of 3,3',4,4'-biphenyltetracarboxylic acid selectively. The first step is preferably started by adding the catalyst components to an o-phthalic diester at a temperature of approximately 100° C. or lower.

In place of the powder palladium salt, a powdery chelate compound formed of a palladium salt and a basic bidentate ligand compound can be utilized if the powdery chelate compound has a specific surface area defined for the powdery palladium salt.

Details of the o-phthalic diester, palladium salt, basic bidentate ligand compound, and copper salt are described in Japanese Patent Publication No. 62-33221, except for the physical properties such as specific surface area of the palladium salt.

Examples of the o-phthalic diesters include di-lower alkyl(C$_1$ to C$_5$) esters of o-phthalic acid such as dimethyl o-phthalate and dipropyl o-phthalate. Examples of the basic bidentate ligand compounds include 1,10-phenanthroline and α,α'-dipyridyl. Examples of the copper salts include a copper salt of a dicarboxylic acid and a copper chelate salt. Most preferred copper salt is copper acetate.

In the course of performing the dimerization reaction or after the dimerization reaction, at least one component of the catalyst composition is supplemented to the reaction mixture. For the powdery palladium salt, the addition of the catalyst component(i.e., palladium salt) is preferably performed to keep the content of the catalyst component in the reaction mixture at a level in the range of 0.0001 to 0.1 molar amount based on the amount of the o-phthalic diester. Per one molar amount of the powdery palladium salt, the basic bidentate ligand compound is added to keep its amount in the range of 0.01 to 5 molar amounts. If a copper salt is utilized, the copper salt is added to the reaction mixture to keep its content in the reaction mixture in the range of 0.01 to 5 molar amounts based on one molar amount of the palladium salt.

The supplemental addition of the catalyst component(s) is preferably performed by adding a combination of the powdery palladium salt and the basic bidentate ligand compound. Preferably, the copper salt is also supplemented.

The supplemental addition of the catalyst component(s) is preferably performed one to ten times.

The supplemental addition of the catalyst component(s) in the second step and the following steps is preferably made to a portion of a reaction mixture comprising the o-phthalic diester, the catalyst composition, and the prepared tetraester of 3,3',4,4'-biphenyltetracarboxylic acid which is separated from other portion of the reaction mixture, and then combined with the other portion of the reaction mixture. The reaction mixture may contain by-products. The supplemental catalyst component(s) are preferably added to the reaction mixture in the form of a suspension in a liquid o-phthalic diester.

There are no specific limitations with respect to the amounts of the catalyst component(s) to be supplemented. However, the supplemental amount preferably is in the range of 0.05 to 5 molar amounts based on one molar amount of the initially added component for each component.

After the dimerization reaction performed in the multiple steps is complete, the desired tetraester of 3,3',4,4'-biphenyltetracarboxylic acid and the palladium salt (which may be converted to metallic palladium or other palladium compounds) is recovered from the reaction mixture. The tetraester of 3,3',4,4'-biphenyltetracarboxylic acid can be separated and purified by a known method such as distillation or crystallization, described, for instance, in Japanese Patent Publications No. 6-43372, No. 6-62508, and No. 6-2715.

The obtained tetraester of 3,3',4,4'-biphenyltetracarboxylic acid can be hydrolyzed at a high temperature and a high pressure or by addition of an acid or an alkaline compound to give 3,3',4,4'-biphenyltetracarboxylic acid. The 3,3',4,4'-biphenyltetracarboxylic acid can be heated to a high temperature such as 250 to 400° C. in the presence of an inert gas or under reduced pressure to perform a dehydration reaction to give 3,3',4,4'-biphenyltetracarboxylic dianhydride.

According to the process of the invention, a tetraester of 3,3',4,4'-biphenyltetracarboxylic acid can be produced from an o-phthalic diester in a high Pd yield (i.e., a molar amount of the produced tetraester of 3,3',4,4'-biphenyltetracarboxylic acid based on one molar amount of Pd contained in the whole palladium salt used in the dimerization reaction). Further, production of by-products such as a tetraester of 2,3,3',4'-biphenyltetracarboxylic acid, low-boiling products (e.g., benzoic ester), and medium-boiling products decreases. Furthermore, the deposition of a metallic palladium onto a wall of a reaction vessel decreases.

The present invention is further described by the following examples.

EXAMPLE 1

In a 10 $m^3$-volume reaction vessel equipped with a stirrer, an inlet for starting material, an outlet for product, an air inlet, and a line for circulating the reaction mixture (which was composed of a circulating pump and a manual catalyst injector, dimerization reaction was carried out in the following manner.

In the reaction vessel, 6.4 $m^3$ (7616 kg, 39.26 kmol.) of dimethyl o-phthalate (referred to as "DMP") was placed. The dimethyl o-phthalate was heated to 80° C. To the heated dimethyl o-phthalate were added 845 g (4.69 mol.) of o-phenanthroline, 960 g (4.29 mol.) of a powdery palladium acetate [specific surface area (BET): 1.34 $m^2$/g, water content (measured at a room temperature to 120° C.): 0.11 wt. %], and 1,006 g (3.85 mol.) of copper acetylacetonate. The resulting mixture was heated to 237±3° C. for 2 hours under stirring, for performing reaction.

Subsequently, both of the same o-phenanthroline (845 g) and the same powdery palladium acetate (960 g) were added to the reaction mixture. The mixture was then subjected to the reaction under stirring for 2 hours.

Subsequently, both of the same o-phenanthroline (845 g) and the same powdery palladium acetate (960 g) were again added to the reaction mixture. The mixture was then subjected to the reaction under stirring for 6 hours.

After the three-step dimerization reaction was complete, the reaction mixture was analyzed by gas chromatography. The analysis gave the following results.

Conversion of DMP: 16.9%

Selectivity to s-DM (tetramethyl 3,3',4,4'-biphenyltetracarboxylate): 80.5%

Yield of s-DM: 208 molar times (per Pd)

Concentration of s-DM in the reaction mixture: 13.6% s-DM/a-DM (molar ratio): 10.1

(a-DM: tetramethyl 2,3,3',4'-biphenyltetracarboxylate)

Pd deposition to reaction vessel: 0.1 kg/one batch

EXAMPLE 2

The procedures of Example 1 were repeated except for replacing the powdery palladium acetate (specific surface area: 1.34 $m^2$/g) with a powdery palladium acetate (specific surface area: 0.70 $m^2$/g), to carry out the dimerization reaction.

After the three-step dimerization reaction was complete, the reaction mixture was analyzed by gas chromatography. The analysis gave the following results.

Conversion of DMP: 16.9%

Selectivity to s-DM: 71.6%

Yield of s-DM: 185 molar times (per Pd)

Concentration of s-DM in the reaction mixture: 12.1% s-DM/a-DM (molar ratio): 9.7

Pd deposition to reaction vessel: 0.3 kg/one batch

EXAMPLE 3

The procedures of Example 1 were repeated except for replacing the powdery palladium acetate (specific surface area: 1.34 m$^2$/g) with a powdery palladium acetate (specific surface area: 2.04 m$^2$/g, water content: 0.29%) and using an automatic catalyst injector, to carry out five-step dimerization reaction in the same manner.

After the five-step dimerization reaction was complete, the reaction mixture was analyzed by gas chromatography. The analysis gave the following results.

Conversion of DMP: 15.8%
Selectivity to s-DM: 75.9%
Yield of s-DM: 183 molar times (per Pd)
Concentration of s-DM in the reaction mixture: 12.0%
s-DM/a-DM (molar ratio): 11.2
Pd deposition to reaction vessel: 0.1 kg/one batch The above-mentioned results of Example 3 indicate that the dimerization reaction could be further continued giving satisfactory results.

What is claimed is:

1. A process for the preparation of a tetraester of 3,3',4,4'-biphenyltetracarboxylic acid which comprises a step of dimerizing an o-phthalic diester in the presence of a catalyst composition comprising a powdery palladium salt having a specific surface area of at least 0.5 m$^2$/g and a basic bidentate ligand compound and one or more steps of continuing the dimerization after supplemental addition of at least one of the powdery palladium salt and the basic bidentate ligand compound.

2. The process of claim 1, wherein the powdery palladium salt has a specific surface area of 0.7 to 20 m$^2$/g.

3. The process of claim 1, wherein the powdery palladium salt has a specific surface area of 1.0 to 10 m$^2$/g.

4. The process of claim 1, wherein the powdery palladium salt is a palladium acetate powder.

5. The process of claim 1, wherein the basic bidentate ligand compound is 1,10-phenanthroline.

6. The process of claim 1, wherein the catalyst composition is formed of a powdery palladium salt and a basic bidentate ligand compound and further a copper salt.

7. The process of claim 6, wherein the copper salt is copper acetylacetonate.

8. The process of claim 1, wherein both of the powdery palladium salt and the basic bidentate ligand compound are supplemented in the continued step.

9. The process of claim 1, wherein the supplemental addition of at least one of the powdery palladium salt and the basic bidentate ligand compound in the second step is made to a portion of a reaction mixture comprising the o-phthalic diester, the catalyst composition, and the prepared tetraester of 3,3',4,4'-biphenyltetracarboxylic acid which is separated from other portion of the reaction mixture and then combined with the other portion of the reaction mixture.

* * * * *